United States Patent
Hoffman et al.

(10) Patent No.: US 12,370,159 B2
(45) Date of Patent: Jul. 29, 2025

(54) COMPOSITIONS AND METHODS OF USE OF BETA-HYDROXY-BETA-METHYLBUTYRATE (HMB) AND PROBIOTICS

(71) Applicant: Metabolic Technologies, Inc., Ames, IA (US)

(72) Inventors: Jay Hoffman, Oviedo, FL (US); John Rathmacher, Story City, IA (US)

(73) Assignee: Metabolic Technologies, LLC, Missoula, MT (US)

( * ) Notice: Subject to any disclaimer, the term of this patent is extended or adjusted under 35 U.S.C. 154(b) by 334 days.

(21) Appl. No.: 16/877,167

(22) Filed: May 18, 2020

(65) Prior Publication Data

US 2020/0276143 A1 Sep. 3, 2020

Related U.S. Application Data

(63) Continuation-in-part of application No. 15/789,104, filed on Oct. 20, 2017, now abandoned.

(60) Provisional application No. 62/411,200, filed on Oct. 21, 2016.

(51) Int. Cl.
*A61K 31/19* (2006.01)
*A61K 35/742* (2015.01)
*A61K 35/747* (2015.01)

(52) U.S. Cl.
CPC ............ *A61K 31/19* (2013.01); *A61K 35/742* (2013.01); *A61K 35/747* (2013.01)

(58) Field of Classification Search
CPC ........... A61K 35/742; A61K 2035/115; A61K 31/19; A61K 35/747; A61K 35/745
See application file for complete search history.

(56) References Cited

U.S. PATENT DOCUMENTS

| | | |
|---|---|---|
| 2010/0179112 A1 | 7/2010 | Rathmacher et al. |
| 2012/0053240 A1* | 3/2012 | Rathmacher ............ A61P 25/00 514/557 |
| 2016/0021921 A1 | 1/2016 | Davis et al. |
| 2016/0037815 A1 | 2/2016 | Walton et al. |
| 2016/0038457 A1 | 2/2016 | Garvey et al. |
| 2016/0066610 A1 | 3/2016 | Garvey et al. |

FOREIGN PATENT DOCUMENTS

| | | | |
|---|---|---|---|
| JP | 2010132585 A | 6/2010 | |
| JP | 2016-520050 | 7/2016 | |
| WO | WO-2012135499 A1 * | 10/2012 | ............... C12N 1/20 |
| WO | 2014099904 | 6/2014 | |
| WO | 2014144458 A1 | 9/2014 | |
| WO | 2014152016 A1 | 9/2014 | |
| WO | 2014179526 A1 | 11/2014 | |
| WO | 2015105981 A2 | 7/2015 | |

OTHER PUBLICATIONS

Townsend et al. β-Hydroxy-β-methylbutyrate (HMB)-free acid attenuates circulating TNF-α and TNFR1 expression postresistance exercise. J Appl Physiol. 2013;115:1173-1182.*
Hoffman et al., "Beta-Hydroxy-Beta-Methylbutyrate attentuates cytokine response during sustained military training", "Nutrition Research", Feb. 21, 2016, pp. 553-563, vol. 36.
Jager et al., "Probiotic *Bacillus coagulans* GBI-30, 6086 reduces exercise-induced muscle damage and increases recovery", "Peer Journal", Jul. 21, 2016, pp. 1-14, vol. 4.
Shreeram et al., "The Relative Bioavailabilty of the Calcium Salt of Beta-Hydroxy-Beta-Methylbutyrate is Greater than that of the Free Fattcy Acid Form in Rats", "The Journal of Nutrition", Oct. 1, 2014, pp. 1549-1555, vol. 144.
Anonymous, "The Effects of Probiotic and HMB Supplementation on Immune Digestive Function in Special Operation", "History of Changes for Study: NCT02762968", May 3, 2016.
Gepner et al., "Combined Effect of *Bacillus coagulans* GBI-30, 6086 and HMB Supplementation on Muscle Integrity and Cytokine Response During Intense Military Training", "Journal of Applied Physiology", Nov. 18, 2017, pp. 11-18, vol. 123, No. 1.
"Perfect Smoothie Protein", https://www.bodyfit.mpn.com, Jul. 5, 2021.
Igarashi, Osamu , et al., "Definition of "digestibility" and "availability"", Maruzen Food Comprehensive Dictionary, Mar. 25, 1998, pp. 512-513; pp. 1147.
Nogushi, Tadashi , "Definition of "biological effectiveness (bioavailablity, biologic availability, biological availability"", Dictionary of Nutrition and Biochemistry; Ed. 3, Mar. 25, 2012, 351.

* cited by examiner

*Primary Examiner* — Lynn Y Fan
(74) *Attorney, Agent, or Firm* — Dentons Davis Brown; Emily E. Harris

(57) ABSTRACT

The present invention provides a composition comprising HMB and at least one probiotic. Methods of administering HMB and at least one probiotic to an animal are also described. HMB and probiotics are administered to attenuate inflammatory cytokine markers and/or maintain muscle integrity.

13 Claims, 5 Drawing Sheets

Figure 1: Post-Pre Changes in the Inflammatory Cytokine Response to Intense Military Training Following 40-Days of Supplementation. CaHMBBC30 = Calcium HMB and Bacillus coagulans; CaHMBPL = Calcium HMB and placebo; CTL = control; * = $p < 0.05$. Results are reported as mean ± SD.

Figure 2: Post-Pre Changes in DTI Measures Following 40-Days of Supplementation and Intense Military Training. DTI = Densor Tensor Imaging; CaHMBBC30 = Calcium HMB and Bacillus coagulans; CaHMBPL = Calcium HMB. Results are reported as mean ± SD.

Effect of multi-strain (non-spore forming) probiotic supplementation on HMB kinetics

COMPOSITIONS AND METHODS OF USE OF BETA-HYDROXY-BETA-METHYLBUTYRATE (HMB) AND PROBIOTICS

This application is a continuation-in-part of U.S. patent application Ser. No. 15/789,104 filed Oct. 20, 2017 which the claims the benefit of U.S. Provisional Patent Application No. 62/411,200 filed Oct. 21, 2016 and herein incorporates U.S. Provisional Patent Application No. 62/411,200 by reference.

BACKGROUND OF THE INVENTION

1. Field

The present invention relates to a composition comprising β-hydroxy-β-methylbutyrate (HMB) and probiotics and methods of using the composition to attenuate inflammatory cytokine markers and/or maintain muscle integrity.

2. Background

HMB

Alpha-ketoisocaproate (KIC) is the first major and active metabolite of leucine. A minor product of KIC metabolism is β-hydroxy-β-methylbutyrate (HMB). HMB has been found to be useful within the context of a variety of applications. Specifically, in U.S. Pat. No. 5,360,613 (Nissen), HMB is described as useful for reducing blood levels of total cholesterol and low-density lipoprotein cholesterol. In U.S. Pat. No. 5,348,979 (Nissen et al.), HMB is described as useful for promoting nitrogen retention in humans. U.S. Pat. No. 5,028,440 (Nissen) discusses the usefulness of HMB to increase lean tissue development in animals. Also, in U.S. Pat. No. 4,992,470 (Nissen), HMB is described as effective in enhancing the immune response of mammals. U.S. Pat. No. 6,031,000 (Nissen et al.) describes use of HMB and at least one amino acid to treat disease-associated wasting.

The use of HMB to suppress proteolysis originates from the observations that leucine has protein-sparing characteristics. The essential amino acid leucine can either be used for protein synthesis or transaminated to the α-ketoacid (α-ketoisocaproate, KIC). In one pathway, KIC can be oxidized to HMB and this accounts for approximately 5% of leucine oxidation. HMB is superior to leucine in enhancing muscle mass and strength. The optimal effects of HMB can be achieved at 3.0 grams per day when given as calcium salt of HMB, or 0.038 g/kg of body weight per day, while those of leucine require over 30.0 grams per day.

Once produced or ingested, HMB appears to have two fates. The first fate is simple excretion in urine. After HMB is fed, urine concentrations increase, resulting in an approximate 20-50% loss of HMB to urine. Another fate relates to the activation of HMB to HMB-CoA. Once converted to HMB-CoA, further metabolism may occur, either dehydration of HMB-CoA to MC-CoA, or a direct conversion of HMB-CoA to HMG-CoA, which provides substrates for intracellular cholesterol synthesis. Several studies have shown that HMB is incorporated into the cholesterol synthetic pathway and could be a source for new cell membranes that are used for the regeneration of damaged cell membranes. Human studies have shown that muscle damage following intense exercise, measured by elevated plasma CPK (creatine phosphokinase), is reduced with HMB supplementation within the first 48 hrs. The protective effect of HMB lasts up to three weeks with continued daily use. Numerous studies have shown an effective dose of HMB to be 3.0 grams per day as CaHMB (calcium HMB) (~38 mg·kg body weight$^{-1}$·day$^{-1}$). HMB has been tested for safety, showing no side effects in healthy young or old adults. HMB in combination with L-arginine and L-glutamine has also been shown to be safe when supplemented to AIDS and cancer patients.

Recently, HMB free acid, a new delivery form of HMB, has been developed. This delivery form has been shown to be absorbed quicker and have greater tissue clearance than CaHMB. The new delivery form is described in U.S. Patent Publication Serial No. 20120053240 which is herein incorporated by reference in its entirety.

HMB has been demonstrated to enhance recovery and attenuate muscle damage from high intensity exercise. HMB attenuates the depression of protein synthesis with TNF-alpha and decreases protein degradation associated with TNF.

In studies examining intense physical activity with minimal recovery, such as that encountered by soldiers during sustained combat operations, the use of HMB supplementation may mitigate the deleterious effects associated with this physical stress. Significant decrements in body mass, strength and power have been reported in soldiers during sustained military operations. These stresses are also associated with significant elevations in inflammatory cytokine marker. A recent field study demonstrated that when HMB is supplemented by soldiers for three weeks during intense training, including simulated combat, the inflammatory response was attenuated, and accompanied by a maintenance of muscle integrity as determined through diffusion tensor imaging. These results were consistent with other investigations reporting that short (e.g., 4 days) and long (e.g., 12-weeks) duration HMB supplementation can attenuate the cytokine response to a muscle damaging protocol.

Probiotics

The use of probiotics as a dietary supplement has become very popular in the past few years for the prevention and treatment of a variety of diseases. Probiotics are live bacteria that are suggested to be beneficial for improving digestive health and immune function, while decreasing inflammation. It is thought that probiotics, such as *Bacillus coagulans*, can enhance enzymatic digestion of foods within the gut resulting in greater absorption of nutrients.

It has been surprisingly and unexpectedly discovered that HMB in combination with probiotics attenuates inflammatory cytokine markers and maintains muscle integrity. A reduction in the cytokine response to intense training has often been used to indicate a more favorable recovery from high intensity training. The combination of HMB and probiotics is synergistic such that the combination results in enhanced absorption of HMB and a greater increase in circulating HMB as compared to administration of HMB alone. This synergism between HMB and probiotics is demonstrated by improved attenuation of inflammatory cytokine markers and muscle integrity as compared to the effects of HMB when administered alone.

SUMMARY OF THE INVENTION

One object of the present invention is to provide a composition for use in maintaining muscle integrity.

Another object of the present invention is to provide a composition for use in attenuating inflammatory cytokine markers.

A further object of the present invention is to provide methods of administering a composition for use in maintaining muscle integrity.

An additional object of the present invention is to provide methods of administering a composition for use in attenuating inflammatory cytokine markers.

Another object of the present invention is to provide methods of improving the absorption of HMB by adding probiotics to a composition containing HMB.

An additional object of the present invention is to provide methods of increasing the time that HMB is in the bloodstream by adding probiotics to a composition containing HMB.

A further object of the present invention is to provide an absorption enhancer for administration with HMB for enhancing the bioavailability of HMB.

Another object of the present invention is to provide an absorption enhancer for administration with HMB for improving the pharmacokinetics of HMB, including the area under the curve and peak plasma levels.

These and other objects of the present invention will become apparent to those skilled in the art upon reference to the following specification, drawings, and claims.

The present invention intends to overcome the difficulties encountered heretofore. To that end, a composition comprising HMB and probiotics is provided. The composition is administered to a subject in need thereof. All methods comprise administering to the animal HMB and probiotics. The subjects included in this invention include humans and non-human mammals. The composition is consumed by a subject in need thereof.

DETAILED DESCRIPTION OF THE INVENTION

Figure 1:
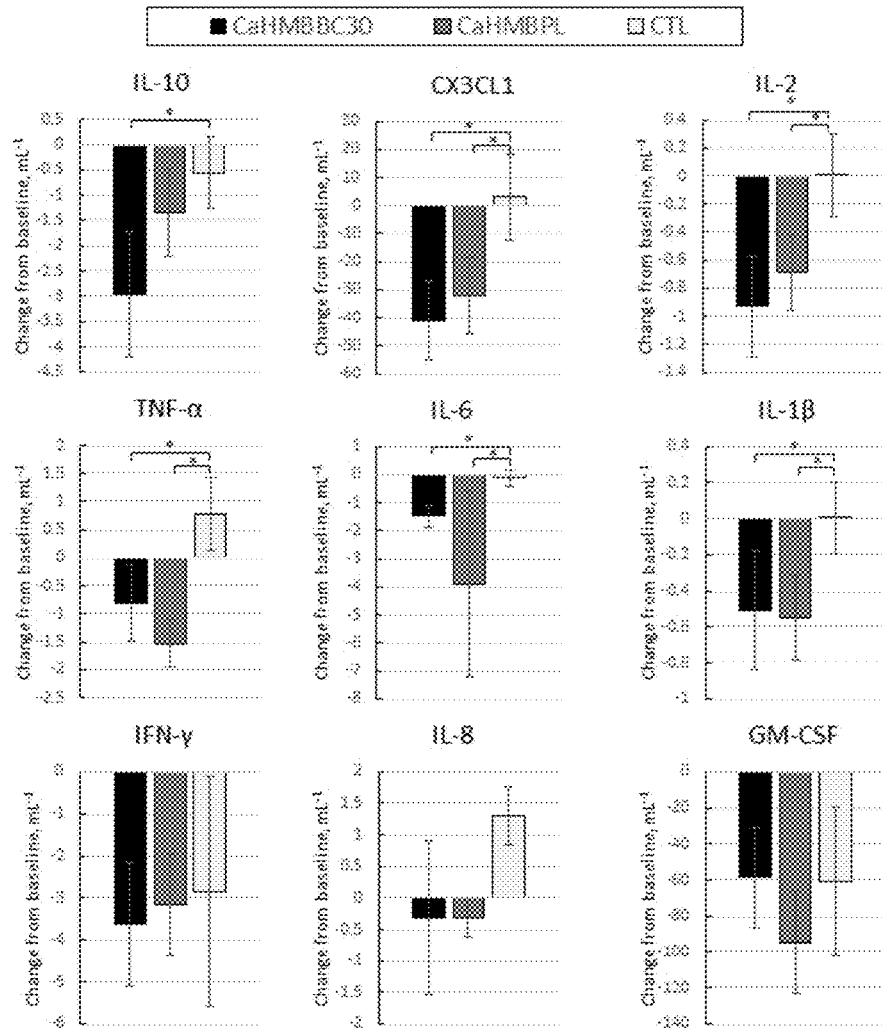
FIG. 1 depicts changes in the inflammatory cytokine response to intense military training following forty (40) days of supplementation.

It has been surprising and unexpectedly discovered that probiotics and HMB have a synergistic relationship. Use of compositions containing HMB and probiotics results in attenuation of inflammatory cytokine markers and maintenance of muscle integrity, and these effects are seen in greater amounts than administration of HMB alone. The combination of HMB and probiotics is synergistic such that the combination results in enhanced absorption of HMB and a greater increase in circulating HMB as compared to administration of HMB alone.

The methods described herein exhibit a synergistic effect of HMB and at least one probiotic. A synergistic effect exists where the action of a combination of active ingredients is greater than the sum of the action of each of the components alone. Therefore, a synergistically effective amount (or an effective amount of a synergistic admixture or combination) is an amount that exhibits a greater effect of HMB than the effect of HMB alone. At least one probiotic is used in synergistic combination with HMB. For example, the synergistic combination has an effect on the bioavailability of HMB which is greater than the effect of HMB when administered alone. Use of at least one probiotic as an absorption enhancer results in a synergistic effect wherein the combination of at least one probiotic with HMB results in an improvement of the bioavailability, pharmacokinetic profile and/or utilization of HMB that is greater than the expected bioavailability, pharmacokinetic profile and/or utilization of HMB when HMB is administered alone.

A synergistically effective amount as used herein includes an amount of two or more compounds that provides the synergistic effect defined above. The two or more compounds include but are not limited to at least one probiotic and HMB in any form or a mixture of forms.

It has been unexpectedly discovered that probiotics act as an absorption enhancer for HMB, thus improving the bioavailability of HMB as compared to administration of HMB alone. Administering probiotics with HMB results in improved peak plasma HMB levels and overall bioavailability, resulting in improved HMB efficiency. Higher bioavailability and efficiency of HMB results in greater effectiveness of HMB when paired with probiotic supplementation. By way of example, combined supplementation of HMB and the probiotic BC30 during intense military training attenuates inflammation and helps maintain muscle integrity better than HMB alone.

The absorption enhancers described herein, including at least one probiotic, provides an increase in the bioavailability of HMB, as measured by such parameters that include but are not limited to area under the curve and peak plasma levels. The absorption enhancer(s) described herein result in a better absorption profile of HMB.

HMB

β-hydroxy-β-methylbutyric acid, or β-hydroxy-isovaleric acid, can be represented in its free acid form as $(CH_3)_2(OH)CCH_2COOH$. The term "HMB" refers to the compound having the foregoing chemical formula, in both its free acid and salt forms, and derivatives thereof. While any form of HMB can be used within the context of the present invention, preferably HMB is selected from the group comprising a free acid, a salt, an ester, and a lactone. HMB esters include methyl and ethyl esters. HMB lactones include isovalaryl lactone. HMB salts include sodium salt, potassium salt, chromium salt, calcium salt, magnesium salt, alkali metal salts, and earth metal salts.

Methods for producing HMB and its derivatives are well-known in the art. For example, HMB can be synthesized by oxidation of diacetone alcohol. One suitable procedure is described by Coffman et al., *J. Am. Chem. Soc.* 80: 2882-2887 (1958). As described therein, HMB is synthesized by an alkaline sodium hypochlorite oxidation of diacetone alcohol. The product is recovered in free acid form, which can be converted to a salt. For example, HMB can be prepared as its calcium salt by a procedure similar to that of Coffman et al. (1958) in which the free acid of HMB is neutralized with calcium hydroxide and recovered by crystallization from an aqueous ethanol solution. The calcium salt of HMB is commercially available from Metabolic Technologies, Ames, Iowa.

Calcium β-Hydroxy-β-Methylbutyrate (HMB) Supplementation

More than 2 decades ago, the calcium salt of HMB was developed as a nutritional supplement for humans. Studies have shown that 38 mg of CaHMB per kg of body weight appears to be an efficacious dosage for an average person.

The molecular mechanisms by which HMB decreases protein breakdown and increases protein synthesis have been reported. Eley et al conducted in vitro studies which have shown that HMB stimulates protein synthesis through mTOR phosphorylation. Other studies have shown HMB decreases proteolysis through attenuation of the induction of the ubiquitin-proteosome proteolytic pathway when muscle protein catabolism is stimulated by proteolysis inducing factor (PIF), lipopolysaccharide (LPS), and angiotensin II. Still other studies have demonstrated that HMB also attenuates the activation of caspases-3 and -8 proteases.

HMB Free Acid Form

In most instances, the HMB utilized in clinical studies and marketed as an ergogenic aid has been in the calcium salt form. Recent advances have allowed the HMB to be manufactured in a free acid form for use as a nutritional supplement. Recently, a new free acid form of HMB was developed, which was shown to be more rapidly absorbed than CaHMB, resulting in quicker and higher peak serum HMB levels and improved serum clearance to the tissues.

HMB free acid may therefore be a more efficacious method of administering HMB than the calcium salt form, particularly when administered directly preceding intense exercise. One of ordinary skill in the art, however, will recognize that this current invention encompasses HMB in any form.

HMB in any form may be incorporated into the delivery and/or administration form in a fashion so as to result in a typical dosage range of about 0.5 grams HMB to about 30 grams HMB.

Any suitable dose of HMB can be used within the context of the present invention. Methods of calculating proper doses are well known in the art. The dosage amount of HMB can be expressed in terms of corresponding mole amount of Ca-HMB. The dosage range within which HMB may be administered orally or intravenously is within the range from 0.01 to 0.2 grams HMB (Ca-HMB) per kilogram of body weight per 24 hours. For adults, assuming body weights of from about 100 to 200 lbs., the dosage amount orally or intravenously of HMB (Ca-HMB basis) can range from 0.5 to 30 grams per subject per 24 hours.

Probiotics

Probiotics, such as *Bacillus coagulans* (BC30), have many health benefits including improving digestive health and immune function and decreasing inflammation. In addition, previous studies have suggested that BC30 can enhance protein absorption. Any probiotic is suitable for use in the composition described herein. Appropriate amounts of *Bacillus coagulans* will be understood by those of skill in the art. A typical composition of the present invention will contain in a one gram dosage formulation from $2\times10^5$ to $10^{10}$ colony forming units of viable bacteria or bacterial spore (in the case of *Bacillus coagulans*). In other embodiments, the amount of bacteria include probiotics at a concentration of from about $1\times10^4$ to about $1\times10^{12}$ viable bacteria. The *Bacillus coagulans* bacteria are in the form of spores, vegetative cells, or a combination thereof. The invention is not limited to any specific probiotic bacteria. Any species of probiotic bacteria can be used in the compositions and methods of the present invention, including but not limited to *Bacillus coagulans, Lactobacillus acidophilus, Bifidobacterium lactis, Lactobacillus plantarum, Lactobacillus casei, Lactobacillus rhamnosus, Lactobacillus paracasei, Bifidobacterium breve, Streptococcus thermophiles, Lactobacillus salivarius,* and *Bifido bacterium longum*.

When the composition is administered orally in an edible form, the composition is preferably in the form of a dietary supplement, foodstuff or pharmaceutical medium, more preferably in the form of a dietary supplement or foodstuff. Any suitable dietary supplement or foodstuff comprising the composition can be utilized within the context of the present invention. One of ordinary skill in the art will understand that the composition, regardless of the form (such as a dietary supplement, foodstuff or a pharmaceutical medium), may include amino acids, proteins, peptides, carbohydrates, fats, sugars, minerals and/or trace elements.

In order to prepare the composition as a dietary supplement or foodstuff, the composition will normally be combined or mixed in such a way that the composition is substantially uniformly distributed in the dietary supplement or foodstuff. Alternatively, the composition can be dissolved in a liquid, such as water.

The composition of the dietary supplement may be a powder, a gel, a liquid or may be tabulated or encapsulated.

Although any suitable pharmaceutical medium comprising the composition can be utilized within the context of the present invention, preferably, the composition is combined with a suitable pharmaceutical carrier, such as dextrose or sucrose.

Furthermore, the composition of the pharmaceutical medium can be intravenously administered in any suitable manner. For administration via intravenous infusion, the composition is preferably in a water-soluble non-toxic form. Intravenous administration is particularly suitable for hospitalized patients that are undergoing intravenous (IV) therapy. For example, the composition can be dissolved in an IV solution (e.g., a saline or glucose solution) being administered to the patient. Also, the composition can be added to nutritional IV solutions, which may include amino acids, glucose, peptides, proteins and/or lipids. The amounts of the composition to be administered intravenously can be similar to levels used in oral administration. Intravenous infusion may be more controlled and accurate than oral administration.

Methods of calculating the frequency by which the composition is administered are well-known in the art and any suitable frequency of administration can be used within the context of the present invention (e.g., one 6 g dose per day or two 3 g doses per day) and over any suitable time period (e.g., a single dose can be administered over a five minute time period or over a one hour time period, or, alternatively, multiple doses can be administered over an extended time period). The composition can be administered over an extended period of time, such as weeks, months or years.

Any suitable dose of HMB and probiotics can be used within the context of the present invention. Methods of calculating proper doses are well known in the art.

It will be understood by one of ordinary skill in the art that HMB and probiotics do not have to be administered in the same composition to perform the claimed methods. Stated another way, separate capsules, pills, mixtures, etc. of probiotics and of HMB may be administered to a subject to carry out the claimed methods.

The term administering or administration includes providing a composition to a mammal, consuming the composition and combinations thereof.

EXPERIMENTAL EXAMPLES

The following examples will illustrate the invention in further detail. It will be readily understood that the composition of the present invention, as generally described and illustrated in the Examples herein, could be synthesized in a variety of formulations and dosage forms. Thus, the following more detailed description of the presently preferred embodiments of the methods, formulations and compositions of the present invention are not intended to limit the scope of the invention, as claimed, but it is merely representative of the presently preferred embodiments of the invention.

Example 1

Methods

Participants

Twenty-six male soldiers from an elite combat unit of the Israel Defense Forces (IDF) volunteered to participate in this double-blind, parallel design study. Following an explanation of all procedures, risks and benefits, each participant provided his informed consent to participate in the study. The Helsinki committee of the IDF Medical Corp and by the Medical Ethics Board and the Helsinki Committee of Soroka Medical Center approved this research study. Participants were not permitted to use any additional dietary supplementation, and did not consume any androgens or other performance enhancing drugs. Screening for performance enhancing drug use and additional supplementation was accomplished via a health questionnaire completed during participant recruitment. Soldiers were from the same unit and were randomly assigned to one of two groups: CaHMB with BC30 (CaHMBBC30; n=9; 20.5±0.8 y; 1.75±0.09 m; 75.4±9.6 kg) or CaHMB with placebo (CaHMBPL, n=9; 19.1±3.4 y; 1.73±0.05 m; 71.4±6.4 kg). A third group of participants from the same unit, who were interested in participating in the study, but were not interested in consuming a supplement agreed to serve as a control group (CTL; n=8; 20.4±0.7 y; 1.73±0.05 m; 68.6±5.3 kg).

Study Protocol

During the 40-day intervention period, all participants performed the same daily protocol. During the first 28 days soldiers were garrisoned on base and participated in the same advanced military training tasks that included combat skill development and conditioning including 90 minutes of intense hand-to-hand combat (krav-maga) training five times a week. The physical training included on average two 5-km runs per week. During weeks 5 and 6 soldiers were in the field and navigated between 25 km-30 km per night in difficult terrain carrying approximately 35 kg of equipment on their back (equating to approximately 40% of participant's body mass). The duration of the navigational exercise lasted between 5-8 hours per evening. During the last evening of training (day 40), the soldiers also performed an additional 5 km stretcher carry following the navigational training. During the final two weeks of training soldiers slept between 5-8 hours per night. All assessments (blood draws and magnetic resonance imaging [MRI]) were conducted in a single day prior to (PRE) and approximately 12-hours following the final supplement consumption (on day 40) (POST). All assessments were performed in the same order at both PRE and POST.

Supplementation Protocol

Participants in both CaHMBBC30 and CaHMBPL ingested 1.0 g of CaHMB three times per day for a total daily consumption of 3 g. Each serving consisted of 4 capsules (250 mg of CaHMB) consumed during morning, noon and evening meals. CaHMB was obtained from Metabolic Technologies Inc. (Ames, IA, USA). The probiotic supplement (*Bacillus coagulans* GBI-30, 6086) was provided by Ganeden Biotech, Inc (Mayfield Hts, OH, USA). Each serving contained $2.0 \times 10^{10}$ colony forming units. Participants consumed one serving per day (morning meal). The placebo was provided by the manufacturer and matched in appearance, weight and taste to the active product. Both the placebo and active product were provided in powder form and mixed in water (~250 ml) prior to ingestion. Participants in CaHMBBC30 and CaHMBPL were provided with two 20-day supplies of HMB and PL. Participants were required to return all used and unused packets at the end of each 20 day period.

Blood Measurements

Resting blood samples were obtained prior to each testing session. All blood samples were obtained following a 15-min equilibration period. These blood samples were obtained from an antecubital arm vein using a 20-gauge disposable needle equipped with a Vacutainer® tube holder (Becton Dickinson, Franklin Lakes, NJ). Each participant's blood samples were obtained at the same time of day during each session following an overnight fast. All blood samples were collected into two Vacutainer® tubes, one containing no anti-clotting agent and the second containing $K_2$EDTA. The blood in the first tube was allowed to clot at room temperature for 30-min and subsequently centrifuged at 3,000×g for 15-min along with the remaining whole blood from the second tube. The resulting plasma and serum was placed into separate 1.8-ml microcentrifuge tubes and frozen at −80° C. for later analysis.

Biochemical Analysis

Serum concentrations of creatine kinase (CK) and lactate dehydrogenase (LDH) were analyzed using a commercially available kinetic assay (Sekisui Diagnostics, Charlottetown, PE, Canada; Sigma-Aldrich, St. Louis, MO, USA), per manufacturer's instructions. Plasma concentrations of cytokines and chemokines included granulocyte-macrophage colony stimulating factor (GM-CSF), fractalkine (CX3CL1), interferon-gamma (INF-γ), interleukin-1beta (IL-3), interleukin-2 (IL-2), interleukin-6 (IL-6), interleukin-8 (IL-8), interleukin-10 (IL-10), and tumor necrosis factor-alpha (TNF-α) were analyzed via multiplex assay, using the human cytokine/chemokine panel one (EMD Millipore, Billerica, MA, USA). In addition, plasma HMB concentrations were analyzed by gas chromatography-mass spectrometry and performed by Metabolic Technologies Inc. using methods previously described. All samples were thawed once and analyzed in duplicate by the same technician using a BioTek Eon spectrophotometer for CK and LDH concentrations (BioTek, Winooski, VT, USA), and MagPix for cytokine and chemokine concentrations (EMD Millipore). Mean intra-assay variability for all assays was below 10%.

Magnetic Resonance Imaging (MRI)

Changes in muscle integrity of the rectus femoris (RF) and vastus lateralis (VL) were assessed using MRI. Due to logistical considerations (element of time), it was determined a priori that the primary focus of the study was to compare the effect of BC30 co-administered with CaHMB to CaHMB only, as such only soldiers in CaHMBBC30 and CaHMBPL were assessed with MRI. Muscle integrity was determined through densor tensor imaging (DTI). DTI is a sensitive MRI technique to assess subclinical signs of muscle injury. DTI assessment is predicated on cell membranes and other structures constraining water diffusion. Water movement can be evaluated by determining the three orthogonal directions of water diffusion, called eigenvectors, and their intensities, called eigenvalues. From the three eigenvalues ($\lambda 1$, $\lambda 2$ and $\lambda 3$), parameters such as fractional anisotropy (FA) and apparent diffusion coefficients (ADC) can be calculated to evaluate the character of water diffusion in a voxel. These measures have been demonstrated to provide information about the integrity of skeletal muscle.

The MRI data were obtained using a 3.0 Tesla whole-body imager (Ingenia, Philips Medical Systems, Best, The Netherlands). During each measure participants were placed supine in the scanner and imaged using phased-array surface coils. A position 20 cm above the patella was chosen as the image center and marked using an oil capsule. All scans were planned axially and consisted of 40 slices of 4 mm width for a foot-head coverage of 160 mm, and a field-of-view of 290×280 mm (RL×AP). Three image acquisitions were performed. A T1w DIXON was used for anatomical reference, a T2w Turbo spin-echo to assess any structural damage to the muscle, and a diffusion tensor imaging (DTI) sequence for muscle fiber tracking. The sequence parameters that were used have been previously published.

Fat suppression (SPAIR—spectrally selective adiabatic inversion recovery) was used for the T2-TSE and DTI scans. The DTI sequence was a 2D-EPI sequence imaged in two packages. The b-value was 400 sec/mm2 and imaged in 15 unique directions. Muscle fiber tracking analysis was calculated by using the Philips 'FiberTrak' software. An ROI (region of interest) was hand drawn for RF and VL on slices 15 and 25. The software then was allowed to delineate the muscle fibers using an algorithm that eliminated tracks if the FA was less than 0.1, if the change in angle was greater than 27° or if the fiber length was less than 10 mm. The same investigator performed all assessments.

Statistical Analyses

Analyses of covariance (ANCOVA) was used to analyze all MRI and blood dependent variables (muscle damage markers and cytokines). PRE and POST values were used as the covariate and dependent variable, respectively. In the event of a significant f ratio, LSD post hoc pairwise comparisons were used to examine the differences among the groups. Results of the ANCOVA were also converted to change from PRE. An alpha level of $p \leq 0.05$ was considered statistically significant for all comparisons. All data are reported as mean±SD unless otherwise noted. Statistical analysis was performed with SPSS (IBM Statistics for Windows, Version 23.0; Armonk, NY: IBM Corp).

Results

Of the 26 solders that participated in this trial, 25 completed the intervention. The only participant who withdrew from the study was injured during training. No side effects associated with supplementation were reported during the study. Based on CaHMB and BC30 consumption (determined by the number of capsules and BC-30 packets returned) compliance for supplementation was 95.0±3.0% among the two CaHMB groups. An additional measure for study compliance was conducted by analyzing plasma HMB concentrations at PRE and POST for participants in both supplement groups. Significant elevations (p=0.010) were noted in plasma HMB concentrations from PRE (3.28±0.73 nmol·L$^{-1}$) to POST (34.1±43.9 nmol·L$^{-1}$) assessments.

Blood Data

Circulating concentrations of inflammatory cytokines can be observed in Table 1. In addition, comparisons of the change from PRE between groups are depicted in FIG. 1. A significant interaction (F=6.48, p=0.006) was observed for changes in circulating TNF-α concentrations. Plasma TNF-α concentrations at POST was significantly lower for CaHMBBC30 and CaHMBPL than CTL (p=0.019 and p=0.002, respectively). However, no differences were noted between CaHMBBC30 and CaHMBPL (p=0.290). A significant interaction (F=4.70, p=0.025) was also noted between the groups for changes in plasma CX3CL1 concentrations. Changes in CX3CL1 concentrations were significantly lower for CaHMBBC30 and CaHMBPL than CTL (p=0.044 and p=0.011, respectively). No differences in CX3CL1 concentrations (P=0.687) were noted between CaHMBBC30 and CaHMBPL. A significant interaction (F=6.93, p=0.006) was noted for changes in plasma IL-1β concentrations. IL-1β concentrations were significantly attenuated for both CaHMBBC30 and CaHMBPL compared to CTL (p=0.005 and p=0.004, respectively). No differences (p=0.878) were observed between CaHMBBC30 and CaHMBPL. A significant interaction (F=4.96, p=0.019) was also found for plasma IL-2 concentrations. Circulating IL-2 concentrations for CaHMBBC30 and CaHMBPL were significantly attenuated at POST compared to CTL (p=0.007 and p=0.029, respectively). No difference (p=0.584) was noted between CaHMBBC30 and CaHMBPL. A significant interaction (F=7.99, p=0.005) was also observed in changes in plasma IL-6 concentrations. Plasma IL-6 concentrations were significantly attenuated in CaHMBBC30 and CaHMBPL compared to CTL (p=0.002 and p=0.018, respectively). No difference (p=0.467) in the IL-6 response at POST was noted between CaHMBBC30 and CaHMBPL. A significant interaction (F=3.72, p=0.041) was also observed in changes in plasma IL-10 concentrations. A significant difference (p=0.013) was seen between CaHMBBC30 and CTL. No other significant differences were noted. No significant interactions were observed for changes in INF-γ (F=1.25, p=0.31), IL-8 (F=1.49, p=0.25) or GM-CSF (F=0.71, p=0.50) concentrations.

TABLE 1

The effect of 40 day of intense military training on cytokine concentrations across study groups.

|  |  | CaHMBBC30 n = 9 | CaHMBPL n = 9 | CTL n = 8 | p value |
|---|---|---|---|---|---|
| TNF-α | Pre | 2.48 ± 1.95 | 2.33 ± 1.31 | 3.08 ± 2.30 | 0.006 |
|  | Post | 1.67 ± 2.01 | 0.81 ± 0.36 | 3.86 ± 2.21 |  |
| CX3CL1 | Pre | 106 ± 63.2 | 81.6 ± 52.3 | 115 ± 64.1 | 0.025 |
|  | Post | 65.1 ± 42.9 | 70.7 ± 29.9 | 118 ± 63.1 |  |
| IL-1β | Pre | 0.95 ± 1.09 | 0.89 ± 0.85 | 1.20 ± 1.03 | 0.006 |
|  | Post | 0.40 ± 0.41 | 0.42 ± 0.37 | 1.21 ± 0.81 |  |
| IL-2 | Pre | 1.58 ± 0.93 | 1.35 ± 1.34 | 2.21 ± 1.81 | 0.019 |
|  | Post | 0.66 ± 0.34 | 0.80 ± 0.87 | 2.21 ± 1.82 |  |
| IL-6 | Pre | 1.87 ± 0.89 | 7.63 ± 17.85 | 2.48 ± 1.42 | 0.005 |
|  | Post | 0.51 ± 0.24 | 5.20 ± 10.68 | 2.34 ± 1.60 |  |
| IL-10 | Pre | 6.85 ± 4.85 | 4.96 ± 4.01 | 9.92 ± 9.77 | 0.041 |
|  | Post | 3.89 ± 2.82 | 3.62 ± 2.64 | 9.37 ± 8.79 |  |
| IFN-γ | Pre | 9.45 ± 6.73 | 11.3 ± 8.31 | 18.2 ± 13.5 | 0.31 |
|  | Post | 5.81 ± 4.75 | 8.11 ± 6.75 | 15.4 ± 11.2 |  |
| IL-8 | Pre | 4.14 ± 6.28 | 2.58 ± 1.05 | 2.53 ± 1.82 | 0.25 |
|  | Post | 3.84 ± 4.11 | 2.27 ± 0.92 | 3.83 ± 2.86 |  |
| GM-CSF | Pre | 232 ± 323 | 170 ± 148.9 | 217 ± 236 | 0.50 |
|  | Post | 173 ± 338 | 75.6 ± 81.6 | 156 ± 144 |  |

CaHMBBC30 = Calcium HMB and *Bacillus coagulan*; CaHMBPL = Calcium HMB and placebo; CTL = control. All data are reported as mean ± SD. ANCOVA test was used to assess differences between groups.

Analysis of muscle damage markers revealed no significant interactions between the groups for plasma LDH (F=0.15, p=0.86) or CK concentrations (F=0.17, p=0.84). No changes in LDH concentrations were noted from PRE (537.7±86.1 IU·L$^{-1}$) to POST (567.5±87.4 IU·L$^{-1}$) in the groups combined. In addition, no change was noted in CK concentrations from PRE (225.4±79.8 IU·L$^{-1}$) to POST (377.6±230.2 IU·L-1) in the groups combined.

DTI

Comparisons of FA and ADC assessments between CaHMBBC30 and CaHMBPL can be observed in Table 2.

TABLE 2

MRI and DTI measures in β-Hydroxy-β-methylbutyrate with and without probiotics (BC30) in response to intense military training

|  |  | Pre | Post | Effect over time P value |
|---|---|---|---|---|
| Rector femoris | | | | |
| Fractional Anisotropy | CaHMBBC30 | 0.24 ± 0.05 | 0.20 ± 0.02 | 0.014 |
|  | CaHMBPL | 0.23 ± 0.02 | 0.19 ± 0.02 |  |
| Apparent Diffusion Coefficient (×10−3 mm$^2$/s) | CaHMBBC30 | 1.79 ± 0.09 | 1.72 ± 0.09 | 0.69 |
|  | CaHMBPE | 1.68 ± 0.06 | 1.77 ± 0.04 |  |
| Vastus lateralis | | | | |
| Fractional Anisotropy | CaHMBBC30 | 0.20 ± 0.03 | 0.21 ± 0.02 | 0.23 |
|  | CaHMBPL | 0.20 ± 0.01 | 0.19 ± 0.01 |  |
| Apparent Diffusion Coefficient (×10−3 mm$^2$/s) | CaHMBBC30 | 1.73 ± 0.05 | 1.71 ± 0.05 | 0.86 |
|  | CaHMBPL | 1.73 ± 0.06 | 1.75 ± 0.12 |  |

All data in the table are reported as mean ± SD. Paired T-test was used to assess changes over time for the both groups. CaHMBBC30 = Calcium HMB and *Bacillus coagulan*; CaHMBPL = Calcium HMB and placebo: CTL = control.

Figure 2:
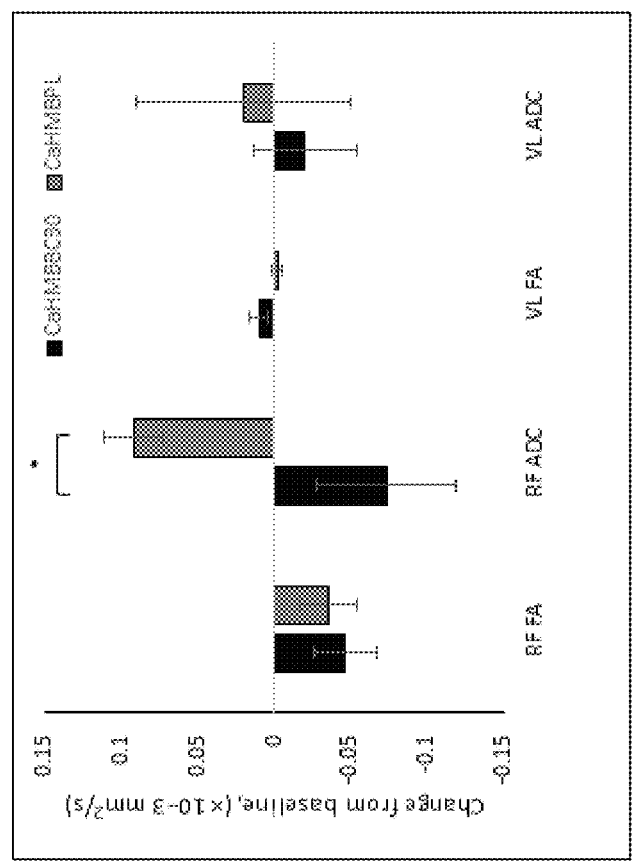
FIG. 2 depicts changes in DTI measure following forty (40) days of supplementation.

In addition, comparisons of the change from PRE between groups is depicted in FIG. 2. No significant difference (F=0.315, p=0.587) in FA was observed between CaHMBBC30 and CaHMBPL in the RF, however, when collapsed across groups a significant decrease was noted from PRE to POST. A significant difference (F=7.198, p=0.023) in ADC was noted between the groups in RF. Participants in CaHMBBC30 experienced a decrease in ADC, while participants in CaHMBPL experienced an increase. No significant differences between the groups were noted in the VL for either FA (F=2.95, p=0.117) or ADC (F=1.886, p=0.200).

The results of this study indicate that 40 days of HMB supplementation with and without *Bacillus coagulans* can attenuate inflammatory cytokine markers during highly intense military training. This combination appeared to attenuate the IL-10 response compared to the control. In addition, the combination of CaHMB and BC30 provided a significant benefit compared to CaHMB alone in maintaining muscle integrity, as indicated by a decrease in apparent diffusion coefficient (ADC) for the rectus femoris (RF).

Plasma HMB for CaHMBPC30, CaHMBPL and CTL were 50.6±15.6 nmol·L$^{-1}$, 15.6±28.0 nmol·L$^{-1}$ and 3.3±0.9 nmol·L$^{-1}$, respectively. The greater HMB concentrations observed for CaHMBBC30 indicates that BC30 has enhanced absorption capability.

Measures of muscle integrity were conducted using DTI, which is considered to be a sensitive method of assessing subclinical signs of muscle injury. DTI measures the diffusion of water molecules and the direction of their movement in a three-dimensional muscle microstructure. In healthy tissue the integrity of the structure results in a barrier to diffusion. Fractional anisotropy (FA) represents the increase in diffusivity into tissue following trauma, while apparent diffusion coefficient (ADC) reflects the degree of diffusion in each direction of the muscle by the length of its axis. A decrease in FA, and an increase in ADC, represent a disruption to the integrity of the muscle indicating greater diffusion. Previously, a significant decreases in FA in both the RF and semitendinosus for placebo group only, and a likely increase in ADC of the VL in the supplement group was reported, indicating that HMB provided in its free acid form may enhance muscle integrity during intense military training. However, the data show that the addition of BC30 to CaHMB provided a synergistic effect for maintaining muscle integrity resulting in a greater degree of muscle protection than that offered by CaHMB alone.

Example 2

A study was conducted to determine whether BC$^{30}$ probiotic supplementation would enhance the bioavailability of HMB (either CaHMB or HMB free acid (HMB-FA). We tested six volunteers before and after two weeks of probiotic supplementation. Between trials, each volunteer took one dose of probiotics (BC$^{30}$) every morning for 14 days. At each trial, baseline plasma HMB levels were measured, then each volunteer was given one serving of HMB (1.0 g of CaHMB or 0.8 g of HMB-FA). Their plasma HMB levels were measured at 2, 5, 10, 15, 25, 35, 45, 60, 90, 120, 150, and 180 min, as well as at 6, 12, and 24 hours.

Figure 3:
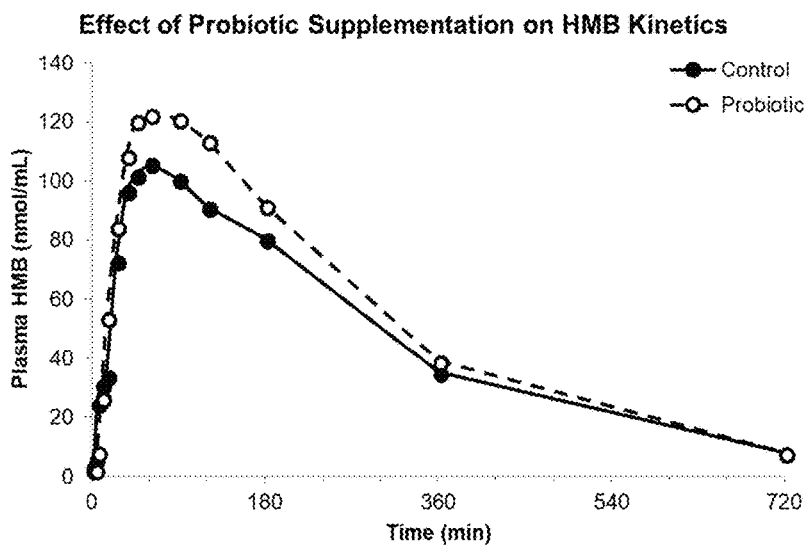
FIG. 3 depicts the effect of probiotic supplementation on HMB kinetics.

In this study, it was found that two weeks of BC$^{30}$ probiotic supplementation increased peak plasma HMB levels by around 15% (p<0.05; see FIG. 3). Probiotic supplementation also increased total HMB exposure (area under the curve) by around 15% (p<0.05; FIG. 3).

Figure 4:
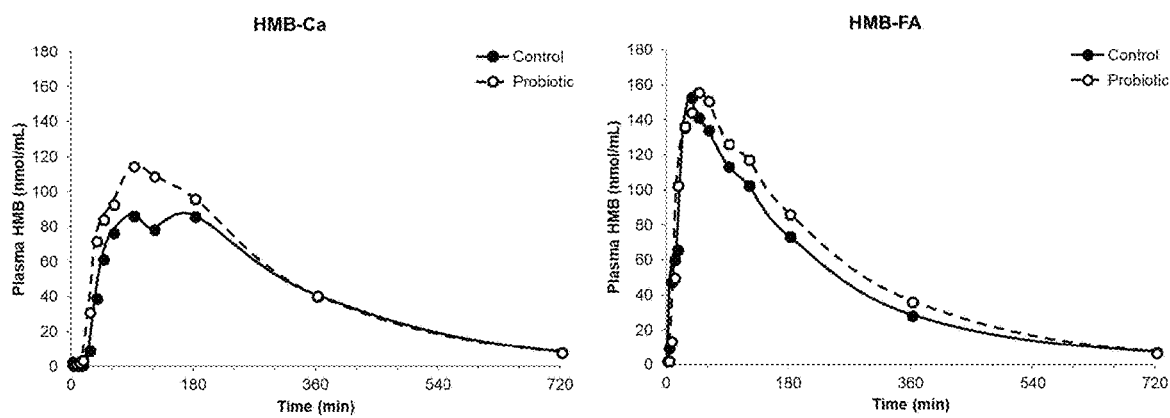
FIG. 4 depicts the effect of calcium HMB and HMB in the free acid form on HMB kinetics.

The pattern of improvement was similar for the CaHMB and HMB-FA formulations, but the probiotic-induced increase in peak plasma HMB levels was larger for CaHMB (see FIG. 4), Probiotic supplementation is especially useful for optimizing exposure to the calcium salt form of HMB.

Probiotic supplementation did not affect the time to reach peak HMB levels, demonstrating that digestion/absorption was more complete and more of the ingested HMB reached the circulation. Importantly, probiotic supplementation also did not affect how much HMB was excreted in urine, demonstrating better utilization of the circulating HMB.

Two weeks of BC$^{30}$ probiotic supplementation improved peak plasma HMB levels and overall bioavailability, demonstrating improved HMB efficiency. Higher bioavailability and efficiency of HMB results in greater effectiveness of HMB when paired with probiotic supplementation.

Example 3

Figure 5:
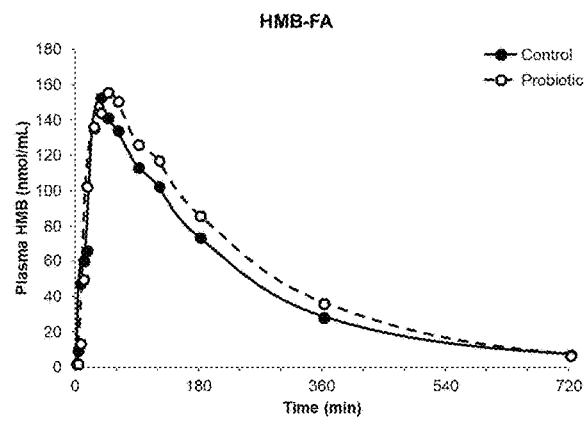
FIG. 5 depicts the effects of multi-strain (non-spore forming) probiotic supplementation on HMB kinetics.

In this study, two weeks of supplementation with a multi-strain probiotic (NOW Foods Probiotic-10 [Blend of 10 Strains: *Lactobacillus acidophilus* (La-14), *Bifidobacterium lactis* (B1-04), *Lactobacillus plantarum* (Lp-115), *Lactobacillus casei* (Lc-11), *Lactobacillus rhamnosus* (Lr-32), *Lactobacillus paracasei* (Lpc-37), *Bifidobacterium breve* (Bb-03), *Streptococcus thermophilus* (St-21), *Lactobacillus salivarius* (Ls-33), *Bifidobacterium longum* (BI-05)) demonstrated that the multi-strain probiotic increased average peak plasma HMB concentration by 11% and increased total HMB exposure by about four (4%) percent. This mixture of probiotics is made of a non-spore forming mix of probiotics. See FIG. 5.

Example 4

Figure 6:
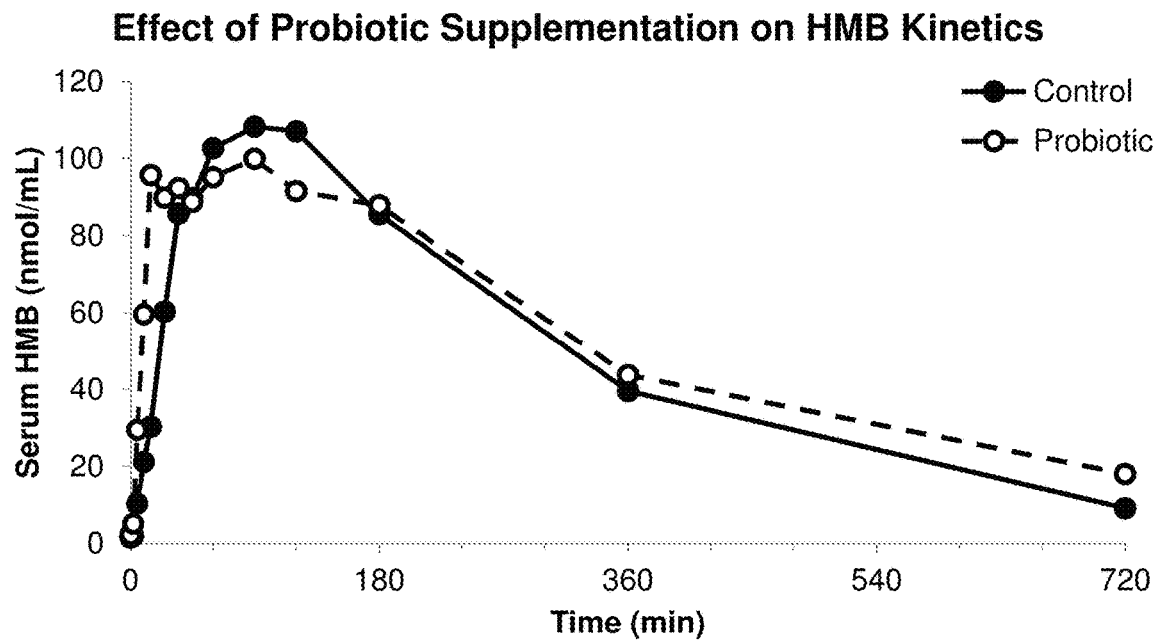
FIG. 6 depicts the effects of LactoSpore probiotics on HMB kinetics.
Figure 7:
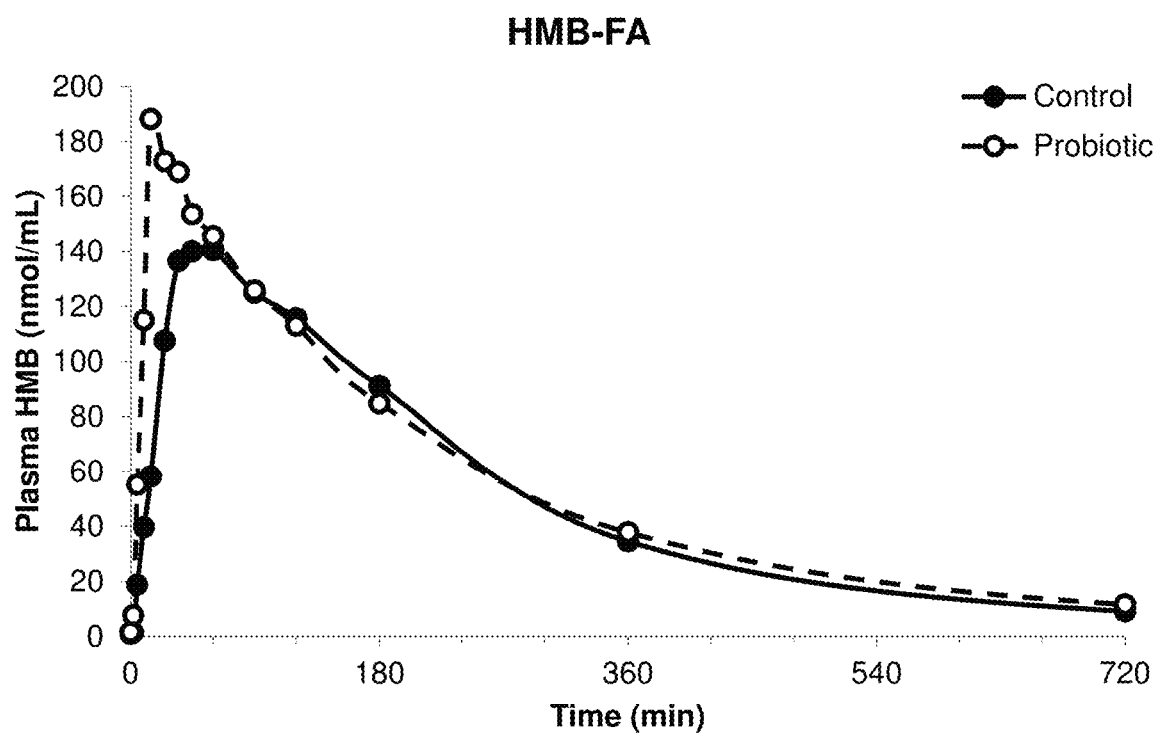
FIG. 7 depicts the effects of probiotic supplementation on HMB free acid kinetics.

In this study, two weeks of supplementation with the spore-forming bacteria *Bacillus coagulans* (Lactospore MTCC 5856) increased average peak plasma HMB concentration by twenty (20%) percent and increased total HMB exposure by around fifteen (15%) percent. See FIG. 6. When subjects given HMB in the free acid form were analyzed separately, peak plasma HMB concentration increased about thirty-six (36%) and total exposure increased 8%. See FIG. 7.

The foregoing description and drawings comprise illustrative embodiments of the present inventions. The foregoing embodiments and the methods described herein may vary based on the ability, experience, and preference of those skilled in the art. Merely listing the steps of the method in a certain order does not constitute any limitation on the order of the steps of the method. The foregoing description and drawings merely explain and illustrate the invention, and the invention is not limited thereto, except insofar as the claims are so limited. Those skilled in the art who have the disclosure before them will be able to make modifications and variations therein without departing from the scope of the invention.

REFERENCES

1. Gonzalez A M, Fragala M S, Jajtner A R, et al. Effects of beta-hydroxy-beta-methylbutyrate free acid and cold water immersion on expression of CR3 and MIP-1beta following resistance exercise. American journal of physiology Regulatory, integrative and comparative physiology. 2014; 306: R483-9.
2. Gonzalez A M, Stout J R, Jajtner A R, et al. Effects of beta-hydroxy-beta-methylbutyrate free acid and cold water immersion on post-exercise markers of muscle damage. Amino acids. 2014; 46: 1501-11.
3. Kraemer W J, Hatfield D L, Volek J S, et al. Effects of amino acids supplement on physiological adaptations to resistance training. Medicine and science in sports and exercise. 2009; 41: 1111-21.
4. Townsend J R, Fragala M S, Jajtner A R, et al. beta-Hydroxy-beta-methylbutyrate (HMB)-free acid attenuates circulating TNF-alpha and TNFR1 expression postresistance exercise. Journal of applied physiology. 2013; 115: 1173-82.
5. van Someren K A, Edwards A J, Howatson G. Supplementation with beta-hydroxy-beta-methylbutyrate (HMB) and alpha-ketoisocaproic acid (KIC) reduces signs and symptoms of exercise-induced muscle damage in man. International journal of sport nutrition and exercise metabolism. 2005; 15: 413-24.
6. Alway S E, Pereira S L, Edens N K, et al. beta-Hydroxy-beta-methylbutyrate (HMB) enhances the proliferation of satellite cells in fast muscles of aged rats during recovery from disuse atrophy. Experimental gerontology. 2013; 48: 973-84.
7. Wilkinson D J, Hossain T, Hill D S, et al. Effects of leucine and its metabolite beta-hydroxy-beta-methylbutyrate on human skeletal muscle protein metabolism. The Journal of physiology. 2013; 591: 2911-23.
8. Giron M D, Vilchez J D, Shreeram S, et al. beta-Hydroxy-beta-methylbutyrate (HMB) normalizes dexamethasone-induced autophagy-lysosomal pathway in skeletal muscle. PloS one. 2015; 10: e0117520.
9. Kimura K, Cheng X W, Inoue A, et al. beta-Hydroxy-beta-methylbutyrate facilitates PI3K/Akt-dependent mammalian target of rapamycin and FoxO1/3a phosphorylations and alleviates tumor necrosis factor alpha/interferon gamma-induced MuRF-1 expression in C2C12 cells. Nutrition research. 2014; 34: 368-74.
10. Eley H L, Russell S T, Tisdale M J. Attenuation of depression of muscle protein synthesis induced by lipopolysaccharide, tumor necrosis factor, and angiotensin II by beta-hydroxy-beta-methylbutyrate. American journal of physiology Endocrinology and metabolism. 2008; 295: E1409-16.
11. Eley H L, Russell S T, Baxter J H, et al. Signaling pathways initiated by beta-hydroxy-beta-methylbutyrate to attenuate the depression of protein synthesis in skeletal muscle in response to cachectic stimuli. American journal of physiology Endocrinology and metabolism. 2007; 293: E923-31.
12. Eley H L, Russell S T, Tisdale M J. Mechanism of attenuation of muscle protein degradation induced by tumor necrosis factor-alpha and angiotensin II by beta-hydroxy-beta-methylbutyrate. American journal of physiology Endocrinology and metabolism. 2008; 295: E1417-26.
13. Pimentel G D, Rosa J C, Lira F S, et al. beta-Hydroxy-beta-methylbutyrate (HMbeta) supplementation stimulates skeletal muscle hypertrophy in rats via the mTOR pathway. Nutrition & metabolism. 2011; 8: 11.
14. Lieberman H R, Bathalon G P, Falco C M, et al. Severe decrements in cognition function and mood induced by sleep loss, heat, dehydration, and undernutrition during simulated combat. Biological psychiatry. 2005; 57: 422-9.
15. Nindl B C, Leone C D, Tharion W J, et al. Physical performance responses during 72 h of military operational stress. Medicine and science in sports and exercise. 2002; 34: 1814-22.
16. McClung J P, Martini S, Murphy N E, et al. Effects of a 7-day military training exercise on inflammatory biomarkers, serum hepcidin, and iron status. Nutrition journal. 2013; 12: 141.
17. Nindl B C, Scofield D E, Strohbach C A, et al. IGF-I, IGFBPs, and inflammatory cytokine responses during gender-integrated Israeli Army basic combat training. Journal of strength and conditioning research/National Strength & Conditioning Association. 2012; 26 Suppl 2: S73-81.
18. Hoffman J R, Gepner Y, Stout J R, et al. beta-Hydroxy-beta-methylbutyrate attenuates cytokine response during sustained military training. Nutrition research. 2016; 36: 553-63.
19. Kraemer W J, Hatfield D L, Comstock B A, et al. Influence of HMB supplementation and resistance training on cytokine responses to resistance exercise. Journal of the American College of Nutrition. 2014; 33: 247-55.
20. Fuller J C, Sharp R L, Angus H F, et al. Comparison of availability and plasma clearance rates of beta-hydroxy-beta-methylbutyrate delivery in the free acid and calcium salt forms. The British journal of nutrition. 2015; 114: 1403-9.
21. Gareau M G, Sherman P M, Walker W A. Probiotics and the gut microbiota in intestinal health and disease. Nature reviews Gastroenterology & hepatology. 2010; 7: 503-14.
22. Sanders M E. Probiotics: definition, sources, selection, and uses. Clinical infectious diseases: an official publication of the Infectious Diseases Society of America. 2008; 46 Suppl 2: S58-61; discussion S144-51.
23. Wang Y, Gu Q. Effect of probiotic on growth performance and digestive enzyme activity of Arbor Acres broilers. Research in veterinary science. 2010; 89: 163-7.
24. Nissen S, Van Koevering M, Webb D. Analysis of beta-hydroxy-beta-methyl butyrate in plasma by gas chromatography and mass spectrometry. Analytical biochemistry. 1990; 188: 17-9.

25. Froeling M, Oudeman J, Strijkers G J, et al. Muscle changes detected with diffusion-tensor imaging after long-distance running. Radiology. 2015; 274: 548-62.
26. Deux J F, Malzy P, Paragios N, et al. Assessment of calf muscle contraction by diffusion tensor imaging. European radiology. 2008; 18: 2303-10.
27. Damon B M, Ding Z, Anderson A W, et al. Validation of diffusion tensor MRI-based muscle fiber tracking. Magnetic resonance in medicine. 2002; 48: 97-104.
28. Vickers A J. The use of percentage change from baseline as an outcome in a controlled trial is statistically inefficient: a simulation study. BMC medical research methodology. 2001; 1: 6.
29. Fuller J C, Jr., Sharp R L, Angus H F, et al. Free acid gel form of beta-hydroxy-beta-methylbutyrate (HMB) improves HMB clearance from plasma in human subjects compared with the calcium HMB salt. The British journal of nutrition. 2011; 105: 367-72.
30. Bouillon R, Van Cromphaut S, Carmeliet G. Intestinal calcium absorption: Molecular vitamin D mediated mechanisms. Journal of cellular biochemistry. 2003; 88: 332-9.
31. Honda H, Gibson G R, Farmer S, et al. Use of a continuous culture fermentation system to investigate the effect of GanedenBC30 (*Bacillus coagulans* GBI-30, 6086) supplementation on pathogen survival in the human gut microbiota. Anaerobe. 2011; 17: 36-42.
32. Portal S, Zadik Z, Rabinowitz J, et al. The effect of HMB supplementation on body composition, fitness, hormonal and inflammatory mediators in elite adolescent volleyball players: a prospective randomized, double-blind, placebo-controlled study. European journal of applied physiology. 2011; 111: 2261-9.
33. Fischer C P. Interleukin-6 in acute exercise and training: what is the biological relevance? Exercise immunology review. 2006; 12: 6-33.
34. Welc S S, Clanton T L. The regulation of interleukin-6 implicates skeletal muscle as an integrative stress sensor and endocrine organ. Experimental physiology. 2013; 98: 359-71.
35. Febbraio M A, Steensberg A, Keller C, et al. Glucose ingestion attenuates interleukin-6 release from contracting skeletal muscle in humans. The Journal of physiology. 2003; 549: 607-12.
36. Lundeland B, Gundersen Y, Opstad P K, et al. One week of multifactorial high-stress military ranger training affects Gram-negative signalling. Scandinavian journal of clinical and laboratory investigation. 2012; 72: 547-54.
37. Henning P C, Scofield D E, Spiering B A, et al. Recovery of endocrine and inflammatory mediators following an extended energy deficit. The Journal of clinical endocrinology and metabolism. 2014; 99: 956-64.
38. Peterson J M, Feeback K D, Baas J H, et al. Tumor necrosis factor-alpha promotes the accumulation of neutrophils and macrophages in skeletal muscle. Journal of applied physiology. 2006; 101: 1394-9.
39. Wojdasiewicz P, Poniatowski L A, Kotela A, et al. The chemokine CX3CL1 (fractalkine) and its receptor CX3CR1: occurrence and potential role in osteoarthritis. Archivum immunologiae et therapiae experimentalis. 2014; 62: 395-403.
40. van Zuiden M, Kavelaars A, Amarouchi K, et al. IL-1beta reactivity and the development of severe fatigue after military deployment: a longitudinal study. Journal of neuroinflammation. 2012; 9: 205.
41. Suzuki K, Nakaji S, Yamada M, et al. Systemic inflammatory response to exhaustive exercise. Cytokine kinetics. Exercise immunology review. 2002; 8: 6-48.
42. Nyangale E P, Farmer S, Cash H A, et al. *Bacillus coagulans* GBI-30, 6086 Modulates *Faecalibacterium prausnitzii* in Older Men and Women. The Journal of nutrition. 2015; 145: 1446-52.
43. Reikeras O. Immune depression in musculoskeletal trauma. Inflammation research: official journal of the European Histamine Research Society [et al]. 2010; 59: 409-14.
44. Lazarus J J, Kay M A, McCarter A L, et al. Viable *Borrelia burgdorferi* enhances interleukin-10 production and suppresses activation of murine macrophages. Infection and immunity. 2008; 76: 1153-62.
45. Peake J M, Della Gatta P, Suzuki K, et al. Cytokine expression and secretion by skeletal muscle cells: regulatory mechanisms and exercise effects. Exercise immunology review. 2015; 21: 8-25.
46. Tidball J G, Villalta S A. Regulatory interactions between muscle and the immune system during muscle regeneration. American journal of physiology Regulatory, integrative and comparative physiology. 2010; 298: R1173-87.
47. Paulsen G, Mikkelsen U R, Raastad T, et al. Leucocytes, cytokines and satellite cells: what role do they play in muscle damage and regeneration following eccentric exercise? Exercise immunology review. 2012; 18: 42-97.
48. Kanda K, Sugama K, Hayashida H, et al. Eccentric exercise-induced delayed-onset muscle soreness and changes in markers of muscle damage and inflammation. Exercise immunology review. 2013; 19: 72-85.
49. Cermak N M, Noseworthy M D, Bourgeois J M, et al. Diffusion tensor MRI to assess skeletal muscle disruption following eccentric exercise. Muscle & nerve. 2012; 46: 42-50.

The invention claimed is:

1. A method for improving the bioavailability of β-hydroxy-β-methylbutyric acid (HMB) in an animal in need thereof, the method comprising administering from about 1 g to about 15 g of β-hydroxy-β-methylbutyric acid (HMB) and at least one absorption enhancer to an animal in need thereof, wherein the absorption enhancer is at least one probiotic and administration of HMB with the absorption enhancer improves the bioavailability of HMB as compared to the bioavailability of HMB administered alone.

2. The method of claim 1, wherein said HMB is selected from the group consisting of its free acid form, its salt, its ester and its lactone.

3. The method of claim 1, wherein said HMB is a calcium salt.

4. The method of claim 1, wherein said HMB is in the free acid form.

5. A method for improving utilization of β-hydroxy-β-methylbutyric acid (HMB) in an animal in need thereof, the method comprising administering a synergistic combination of from about 1 g to about 15 g of β-hydroxy-β-methylbutyric acid (HMB) and an effective amount of at least one absorption enhancer to an animal in need thereof, wherein the at least one absorption enhancer is at least one probiotic and administration of HMB with the at least one absorption enhancer improves muscle integrity as compared to administration of HMB alone.

6. The method of claim 5, wherein said HMB is a calcium salt.

7. The method of claim 5, wherein said HMB is in the free acid form.

8. A method for improving the efficacy of β-hydroxy-β-methylbutyric acid (HMB) comprising administering from about 1 g to about 15 g of HMB with at least one absorption enhancer in synergistic effective amounts, wherein the absorption enhancer is at least one probiotic and administration of HMB with the absorption enhancer improves the efficacy of HMB as compared to efficacy of HMB administered alone.

9. The method of claim 8, wherein said HMB is a calcium salt.

10. The method of claim 8, wherein said HMB is in the free acid form.

11. The method of claim 5, wherein the at least one probiotic is *Bacillus coagulans* GBI-30.

12. The method of claim 5, wherein the at least one probiotic increased the plasma HMB concentration by at least 10% compared to administration of HMB alone.

13. The method of claim 5, wherein the combination of HMB and the at least one probiotic increases the area under the curve (AUC) for plasma HMB concertation by at least 10%.

\* \* \* \* \*